United States Patent
Li et al.

(10) Patent No.: US 12,026,884 B2
(45) Date of Patent: Jul. 2, 2024

(54) METHODS, APPARATUSES AND SYSTEMS FOR SURVIEW SCAN

(71) Applicant: Neusoft Medical Systems Co., Ltd., Liaoning (CN)

(72) Inventors: Shuangxue Li, Liaoning (CN); Jun Yu, Liaoning (CN); Wei Li, Liaoning (CN)

(73) Assignee: Neusoft Medical Systems Co., Ltd., Shenyang (CN)

( * ) Notice: Subject to any disclaimer, the term of this patent is extended or adjusted under 35 U.S.C. 154(b) by 356 days.

(21) Appl. No.: 17/698,679

(22) Filed: Mar. 18, 2022

(65) Prior Publication Data
US 2022/0301166 A1 Sep. 22, 2022

(30) Foreign Application Priority Data
Mar. 19, 2021 (CN) .......................... 202110296787.0

(51) Int. Cl.
*G06T 7/00* (2017.01)
*G06T 7/73* (2017.01)
(Continued)

(52) U.S. Cl.
CPC .............. *G06T 7/0014* (2013.01); *G06T 7/74* (2017.01); *G06V 10/25* (2022.01); *G06V 40/161* (2022.01);
(Continued)

(58) Field of Classification Search
CPC .............. G06T 7/0014; G06T 7/74; G06T 2207/10072; G06T 2207/30201; G06V 10/25; G06V 40/161; G06V 40/19
See application file for complete search history.

(56) References Cited

U.S. PATENT DOCUMENTS

2005/0147198 A1* 7/2005 Kiyono ................ G06T 11/005
378/4
2018/0325489 A1 11/2018 De Beni et al.
(Continued)

FOREIGN PATENT DOCUMENTS

CN 108294772 A 7/2018
CN 109276248 A 1/2019
(Continued)

OTHER PUBLICATIONS

Office Action and Search Report Issued in Chinese Application No. 2021102967870, dated May 16, 2023, 22 pages (Submitted with machine translation).
(Continued)

*Primary Examiner* — Khai M Nguyen
(74) *Attorney, Agent, or Firm* — Fish & Richardson P.C.

(57) ABSTRACT

Methods, apparatuses, and systems for surview scans are provided. In one aspect, a method includes: collecting a static image for a subject on a scan bed when it is stationary; determining a scan beginning position and a reference position in the static image; obtaining a first distance between the scan beginning position and the reference position; during a movement of the scan bed, obtaining a video image of the subject in real time; identifying a corresponding reference position in the video image; marking, according to the corresponding reference position and the first distance, a corresponding scan beginning position in the video image; detecting a second distance between the corresponding scan beginning position and a positioning line in the video image; and in response to detecting that the second distance is equal to or less than a predetermined first threshold, starting the surview scan to obtain a surview image.

20 Claims, 7 Drawing Sheets

(51) Int. Cl.
*G06V 10/25* (2022.01)
*G06V 40/16* (2022.01)
*G06V 40/19* (2022.01)

(52) U.S. Cl.
CPC .... *G06V 40/19* (2022.01); *G06T 2207/10072* (2013.01); *G06T 2207/30201* (2013.01)

(56) References Cited

U.S. PATENT DOCUMENTS

| | | | |
|---|---|---|---|
| 2022/0061781 A1* | 3/2022 | Zhao | A61B 6/547 |
| 2022/0084245 A1* | 3/2022 | Hu | G06T 7/97 |
| 2022/0257209 A1* | 8/2022 | Gagnon | A61B 6/488 |
| 2023/0293132 A1* | 9/2023 | Liu | G06T 7/73 |
| | | | 382/103 |

FOREIGN PATENT DOCUMENTS

| | | |
|---|---|---|
| CN | 111631744 A | 9/2020 |
| CN | 112043302 A | 12/2020 |
| WO | WO2020132958 A1 | 7/2020 |

OTHER PUBLICATIONS

Office Action and Search Report Issued in Chinese Application No. 2021102967870, dated Nov. 7, 2022, 26 pages. (Submitted with Machine/Partial Translation).

Office Action and Search Report Issued in Chinese Application No. 2021102967870, dated Sep. 13, 2023, 23 pages (Submitted with Machine Translation).

* cited by examiner

METHODS, APPARATUSES AND SYSTEMS FOR SURVIEW SCAN

CROSS REFERENCE TO RELATED APPLICATION

This application claims priority to Chinese Patent Application No. 202110296787.0 filed on Mar. 19, 2021, the entire content of which is incorporated herein by reference for all purposes.

TECHNICAL FIELD

The present disclosure relates to the field of medical image processing technologies, and in particular to methods, apparatuses and systems for surview scan.

BACKGROUND

A Computed Tomography (CT) system includes a CT device and a main console. The CT device is located in a scan room to perform CT scan for a subject and the main console is located in an operation room to control the CT device.

The CT system performs a surview scan (may also be referred to as a localizer scan) in the following process including that: firstly, an operation technician performs subject registration and scan protocol selection in the operation room; then, the operation technician enters the scan room to allow the subject to lie on a scan bed, position the subject according to a to-be-scanned region of the subject, light up scan positioning lines of the CT device and confirm that the scan positioning lines of the CT device are emitted onto a scan beginning position of a body surface of the subject; after completing the positioning, the operation technician goes back to the operation room and collects data by operating the CT device to radiate continuously for data collection; at this time, the scan bed carries the subject through a radiation region at a constant speed and a surview image (may also be referred to as a localizer image) is formed through processing.

It can be seen that, in a surview scan process, the operation technician needs to complete positioning through direct contact with the subject. If an infectious disease is carried by the subject, a great healthy risk will be brought to the operation technician.

SUMMARY

According to a first aspect of embodiments of the present disclosure, there is provided a method of a surview scan, which is applied to a computed tomography system. The method includes: collecting a static image for a subject on a scan bed of the computed tomography system when the scan bed is stationary, where the static image includes a positioning line of the computed tomography system; determining, according to received positioning operation information, a scan beginning position for surview scan in the static image as a first scan beginning position; identifying a reference position in the static image as a first reference position; obtaining a first distance between the scan beginning position and the first reference position; during a movement process of the scan bed, obtaining a video image of the subject in real time; identifying a reference position in the video image as a second reference position, the reference position in the video image corresponding to the reference position in the static image; marking, according to the second reference position and the first distance, a scan beginning position in the video image as a second scan beginning position, the scan beginning position in the video image corresponding to the scan beginning position in the static image; detecting a second distance between the second scan beginning position and a positioning line in the video image that corresponds to the positioning line in the static image; and in response to detecting that the second distance is equal to or less than a predetermined first threshold, starting the surview scan to obtain a surview image.

According to a second aspect of embodiments of the present disclosure, there is provided an apparatus for a surview scan, including: a determining module, configured to collect a static image for a subject on a scan bed of a computed tomography system when the scan bed is stationary, where the static image for the subject includes a positioning line of the computed tomography system; determine, according to received positioning operation information, a scan beginning position for surview scan in the static image as a first scan beginning position; identify a reference position in the static image as a first reference position; obtain a first distance between the scan beginning position and the first reference position; an identifying module, configured to, during a movement process of the scan bed, obtain a video image of the subject in real time; identify a reference position in the video image as a second reference position, the reference position in the video image corresponding to the reference position in the static image; a marking module, configured to mark, according to the second reference position and the first distance, a scan beginning position in the video image as a second scan beginning position, the scan beginning position in the video image corresponding to the scan beginning position in the static image; a scan module, configured to detect a second distance between the second scan beginning position and a positioning line in the video image that corresponds to the positioning line in the static image; and in response to detecting that the second distance is equal to or less than a predetermined first threshold, start the surview scan to obtain a surview image.

According to a third aspect of embodiments of the present disclosure, there is provided a system for a surview scan, including a scan bed, a scan gantry, a positioning lamp, a first camera, a second camera, and a main console; where the scan gantry is configured to control the scan bed to move according to a control instruction of the main console; the positioning lamp is configured to generate a positioning line; the first camera is disposed above the scan bed to collect a video image of a subject on the scan bed and send the video image of the subject to the main console; the second camera is disposed in a scan bore on the scan gantry to collect a video image of the positioning line and send the video image of the positioning line to the main console; the main console is configured to perform operations including: collecting a static image for the subject on the scan bed when the scan bed is stationary, where the static image includes the positioning line; determining, according to received positioning operation information, a scan beginning position for a surview scan in the static image as a first scan beginning position; identifying a reference position in the static image as a first reference position; obtaining a first distance between the scan beginning position and the first reference position in the static image; during a movement process of the scan bed, obtaining a video image of the subject in real time; identifying a reference position in the video image as a second reference position, the reference position in the video image corresponding to the reference position in the static image; marking, according to the second reference position and the first distance, a scan beginning position in the video image as a second scan beginning position, the scan beginning position in the video image corresponding to the scan beginning position in the static image; detecting a second distance between the second scan beginning position and the positioning line in the video image that corresponds to the positioning line in the static image; and in response to detecting that the second distance is equal to or less than a predetermined first threshold, starting the surview scan to obtain a surview image.

The foregoing and other aspects or embodiments can each optionally include one or more of the following features, alone or in combination. For example, the reference position in the static image includes a center of a face contour of the subject, and identifying the reference position in the video image as the second reference position includes: capturing, based on a predetermined face contour recognition algorithm, the face contour of the subject in the video image, and determining, according to pixel coordinates corresponding to the face contour captured in the video image, a position of the center of the face contour as the second reference position.

In some embodiments, the reference position in the static image comprises a feature point around the scan beginning position, and identifying the reference position in the video image as the second reference position includes: searching, in the video image, for an image region matching a first image that is a part of the static image comprising the feature point; and determining, according to a position relationship between the feature point in the first image and a contour of the first image, a position of the feature point in the image region as the second reference position.

In some embodiments, the method further includes: displaying, in real time, the surview image in a screen of a main console of the computed tomography system; and in response to determining that the surview image satisfies a predetermined scan requirement, stopping the surview scan.

In some embodiments, the method further includes: during the movement process of the scan bed, identifying an eye position in real time in the video image; and in response to detecting that a third distance between the eye position and the positioning line in the video image is less than or equal to a predetermined second threshold, outputting information for prompting the subject to close eyes.

In some embodiments, the method further includes: in response to detecting that the third distance between the eye position and the positioning line is less than or equal to a predetermined third threshold and that at least one of the eyes of the subject is open, turning off a positioning lamp generating the positioning line, wherein the third threshold is less than the second threshold; and in response to detecting that the third distance between the eye position and the positioning line is greater than the third threshold and that the third distance keeps increasing, turning on the positioning lamp.

In some embodiments, the method further includes: during the movement process of the scan bed, displaying the video image as a global view in a screen of a main console of the computed tomography system, and displaying a collected image including the positioning line as a local view in the screen of the main console.

In some embodiments, the method further includes: during the surview scan, displaying the video image as a global view in a screen of a main console of the computed tomography system, displaying a collected image including the positioning line as a local view in the screen of the main console, and displaying a generated surview image in real time in the screen of the main console.

In some embodiments, the method further includes: in a tomography scan process after the surview scan is stopped, displaying the surview image as a global view in a screen of a main console of the computed tomography system, displaying a collected image including the positioning line as a local view in the screen of the main console, and displaying a generated tomogram in real time in the screen of the main console.

It should be understood that the above general descriptions and subsequent detailed descriptions are merely illustrative and explanatory rather than limiting of the present disclosure.

BRIEF DESCRIPTION OF THE DRAWINGS

The accompanying drawings, which are incorporated in and constitute a part of the present description, illustrated embodiments consistent with the present disclosure and serve to explain the principles of the present disclosure together with the description.

Like reference numbers and designations in the various drawings indicate like elements. It is also to be understood that the various exemplary implementations shown in the figures are merely illustrative representations and are not necessarily drawn to scale.

DETAILED DESCRIPTION OF THE EMBODIMENTS

Figure 1:
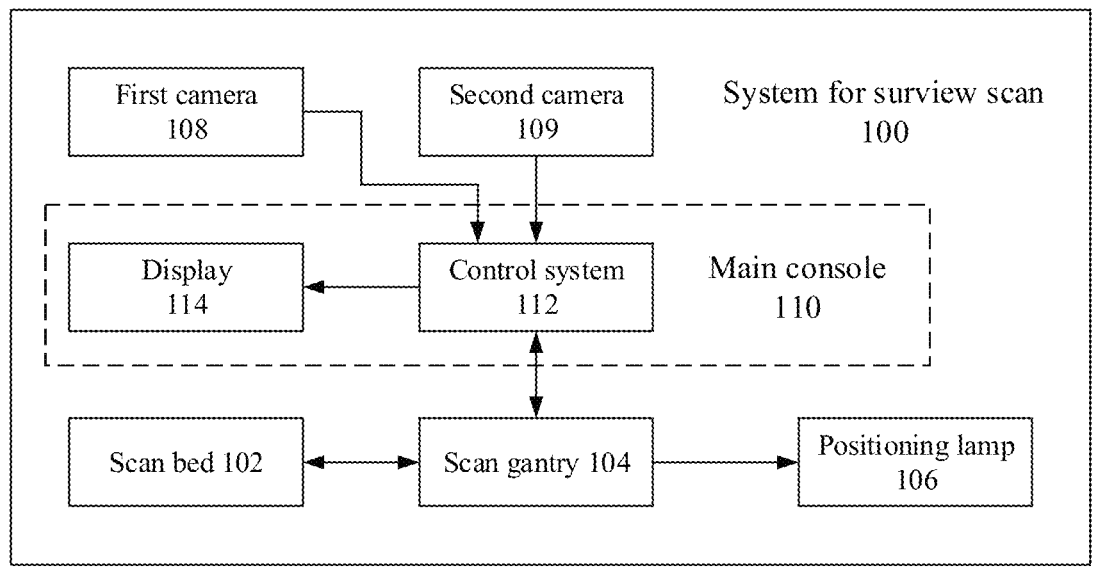
FIG. 1 is a structural example diagram illustrating a system for surview scan according to one or more embodiments of the present disclosure.

Example embodiments will be described in detail herein, with the illustrations thereof represented in the drawings. When the following descriptions involve the drawings, like numerals in different drawings refer to like or similar elements unless otherwise indicated. The embodiments described in the following examples do not represent all embodiments consistent with the present disclosure. Rather, they are merely examples of apparatuses and methods consistent with some aspects of the present disclosure as detailed in the appended claims.

The terms used in the embodiments of the present disclosure are for the purpose of describing particular embodiments only, and are not intended to limit the present disclosure. Terms "a," "the" and "said" in their singular forms in the embodiments of the present disclosure and the appended claims are also intended to include plurality, unless clearly indicated otherwise in the context. It should also be understood that the term "and/or" as used herein refers to and includes any or all possible combinations of one or more of the associated listed items.

It is to be understood that, although the terms "first," "second," "third," and the like can be used in the embodiments of the present disclosure to describe various information, such information should not be limited to these terms. These terms are only used to distinguish the same type of information from each other. For example, without departing from the scope of the present disclosure, the first information can also be referred to as the second information and similarly, the second information can also be referred to as the first information. Depending on the context, the word "if" as used herein can be interpreted as "when" or "upon" or "in response to determining".

A CT scan process for a subject includes two stages: in a first stage, survey scan is performed for the subject with a lower dose radiation to obtain a survey image; and in a second stage, parameter values such as slice thickness and slice gap required for a subsequent CT scan are configured based on the survey image, where a radiation dose used in the second stage is greater than a radiation dose used in the first stage, and tomograms obtained by CT scan in the second stage can be used for disease diagnosis. In a pandemic season of infectious diseases, or in a special application scenario such as a fever clinic in a hospital, it is highly possible that a subject needing to receive a CT scan (e.g., COVID-19 patient) carries an infectious virus, which brings a large risk to the health of persons in contact with the subject. At this time, additional requirements will be proposed for use of medical appliances in a treatment or diagnosis position. Thus, it is highly desirable that an operation technical can complete an entire scan process in an operation room without entering a scan room to be in direct contact with the subject, thereby reducing the risk to the health of the operation technician.

Implements of the present disclosure provide systems for survey scan, which can meet the above requirements. FIG. 1 is a structural example diagram illustrating a system 100 for survey scan according to one or more embodiments of the present disclosure. As shown in FIG. 1, the system 100 for survey scan can include a scan bed 102, a scan gantry 104, a positioning lamp 106, a first camera 108, a second camera 109, and a main console 110. The scan gantry 104 is configured to control the scan bed 102 to move according to a control instruction of the main console 110. The positioning lamp 106 is configured to generate a positioning line. The first camera 108 is disposed above the scan bed 102 to collect a video image of a subject on the scan bed 102 and send the video image of the subject to the main console 110. The second camera is disposed in a scan bore on the scan gantry 104 to collect a video image of the positioning line and send the video image of the positioning line to the main console 110. The main console 110 can be configured to implement a method of survey scan described subsequently.

The scan bed 102 and the scan gantry 104 can be a scan bed and a scan gantry in a medical imaging system, e.g., a CT system or a Positron Emission Tomography Computed Tomography (PET-CT) system.

The main console 110 can include a control system 112 and a display 114.

A field of view of the first camera 108 is to cover the subject on the scan bed 102, and the field of view of the second camera 109 is to cover the entire position line. For example, the first camera 108 can be mounted, for example, on a ceiling above the scan bed 102, or at an upper part of an outer cover of the scan gantry 104 (higher than a position where the subject lies on the scan bed 102). The second camera 109 can be, for example, disposed on the outer cover of the scan gantry 104 (higher than a position where the subject lies on the scan bed) or in the scan gantry 104 for detection of the positioning line.

Figure 2:
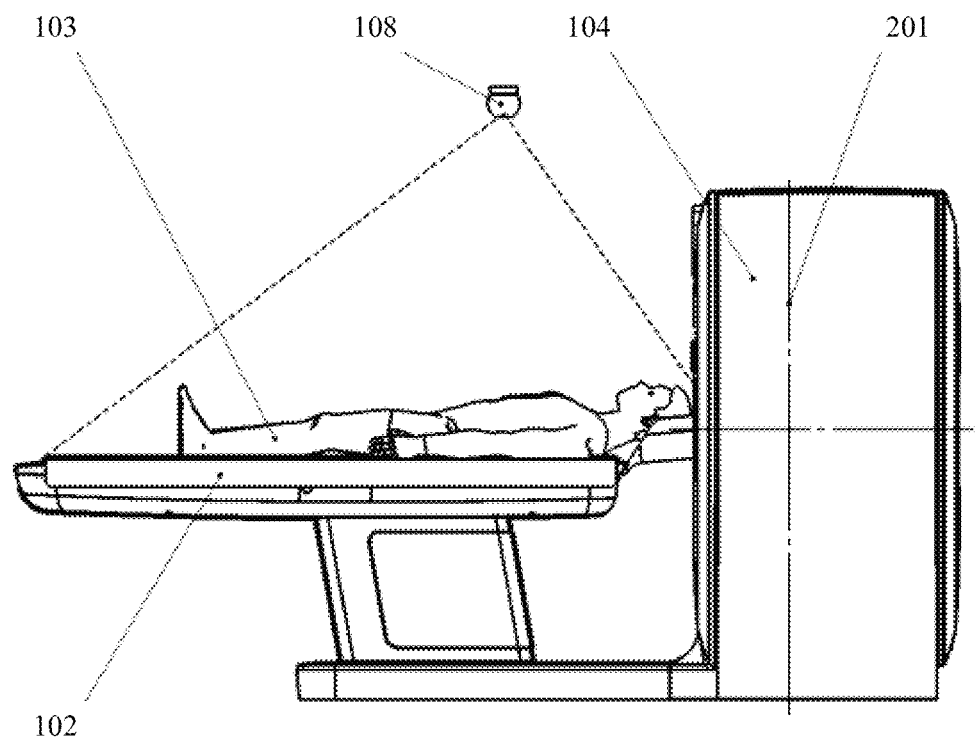
FIG. 2 is a side view illustrating a system for surview scan according to one or more embodiments of the present disclosure.
Figure 3:
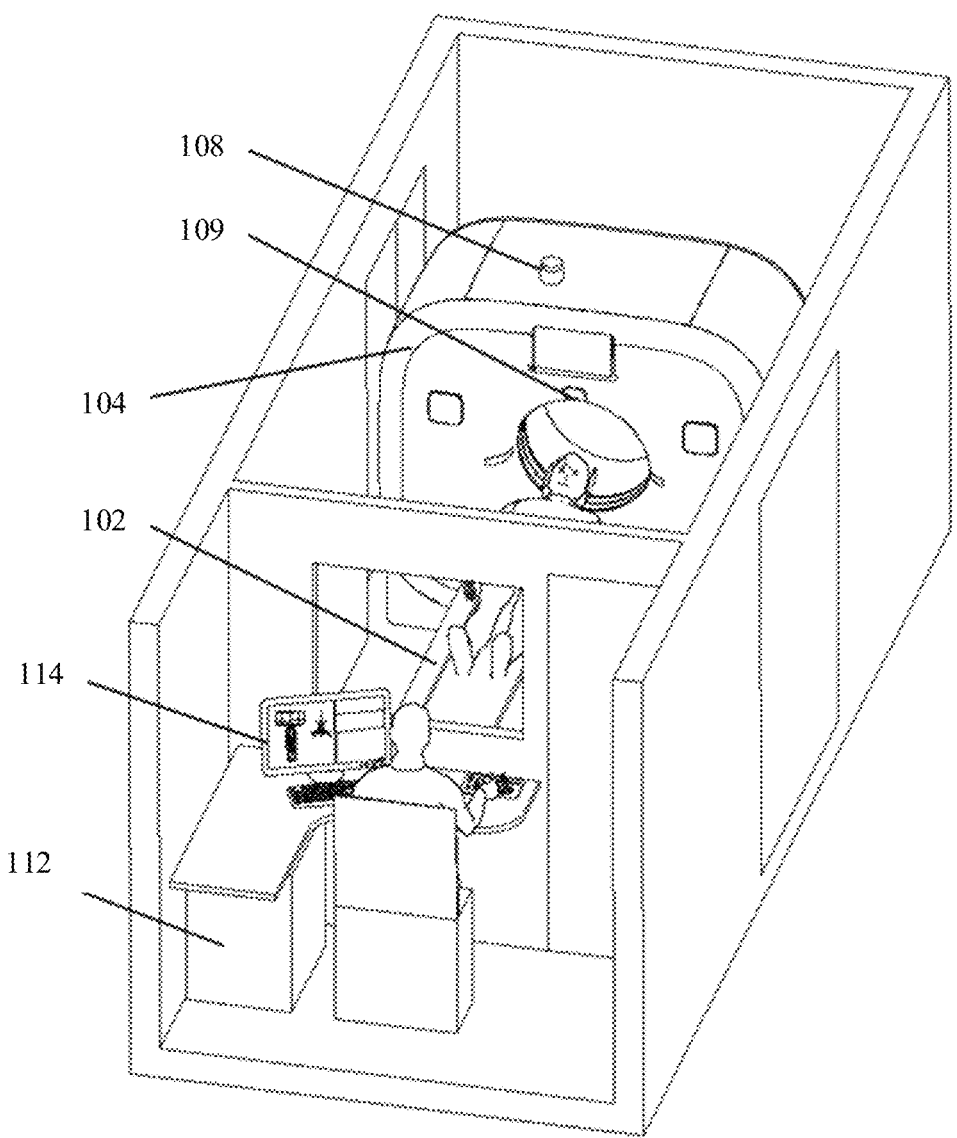
FIG. 3 is an axonometric diagram illustrating the system for surview scan shown in FIG. 2.
Figure 4:
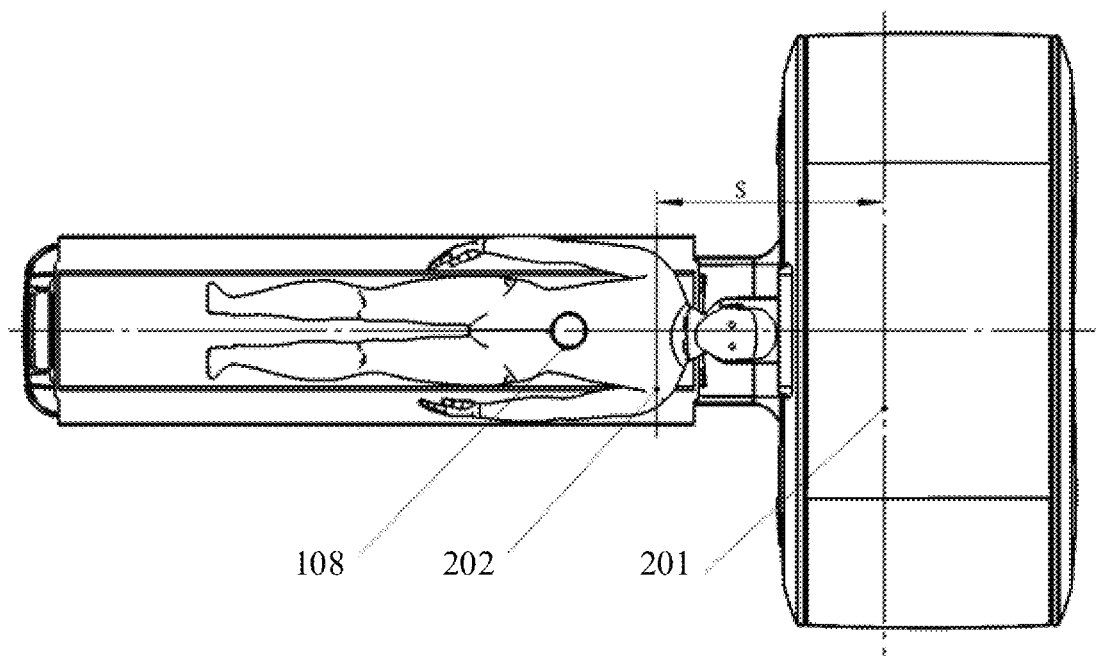
FIG. 4 is a top view illustrating the system for surview scan shown in FIG. 2.
Figure 5:
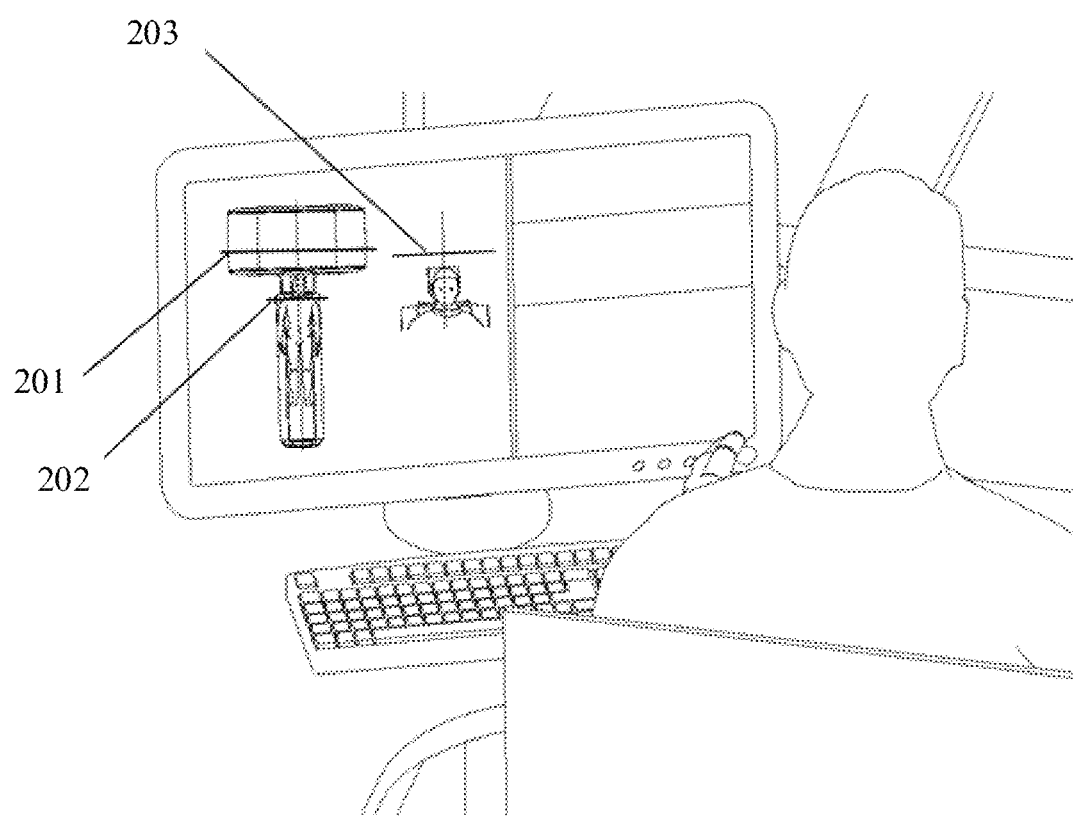
FIG. 5 is a displaying example diagram illustrating a positioning line in a screen of a main console according to one or more embodiments of the present disclosure.

FIGS. 2-5 illustrate a system for survey scan according to one or more embodiments of the present disclosure, where FIG. 2 is a mounting side view of the system, FIG. 3 is an axonometric diagram of the system, FIG. 4 is a top view of the system, and FIG. 5 is a displaying example diagram illustrating a positioning line in a screen of a main console (e.g., the main console 110 of FIG. 1) of the system. The system can be the system 100 of FIG. 1. In FIGS. 2, 3, 4 and 5, reference numbers are list below: a scan gantry 104, a position 201 of a positioning lamp (e.g., the positioning lamp 106 of FIG. 1), a scan bed 102, a subject 103, a first camera 108, a second camera 109, a scan indication line 202, a positioning line 203, and a display 114.

A method of survey scan according to the present disclosure will be described below in details in combination with embodiments.

Figure 6:
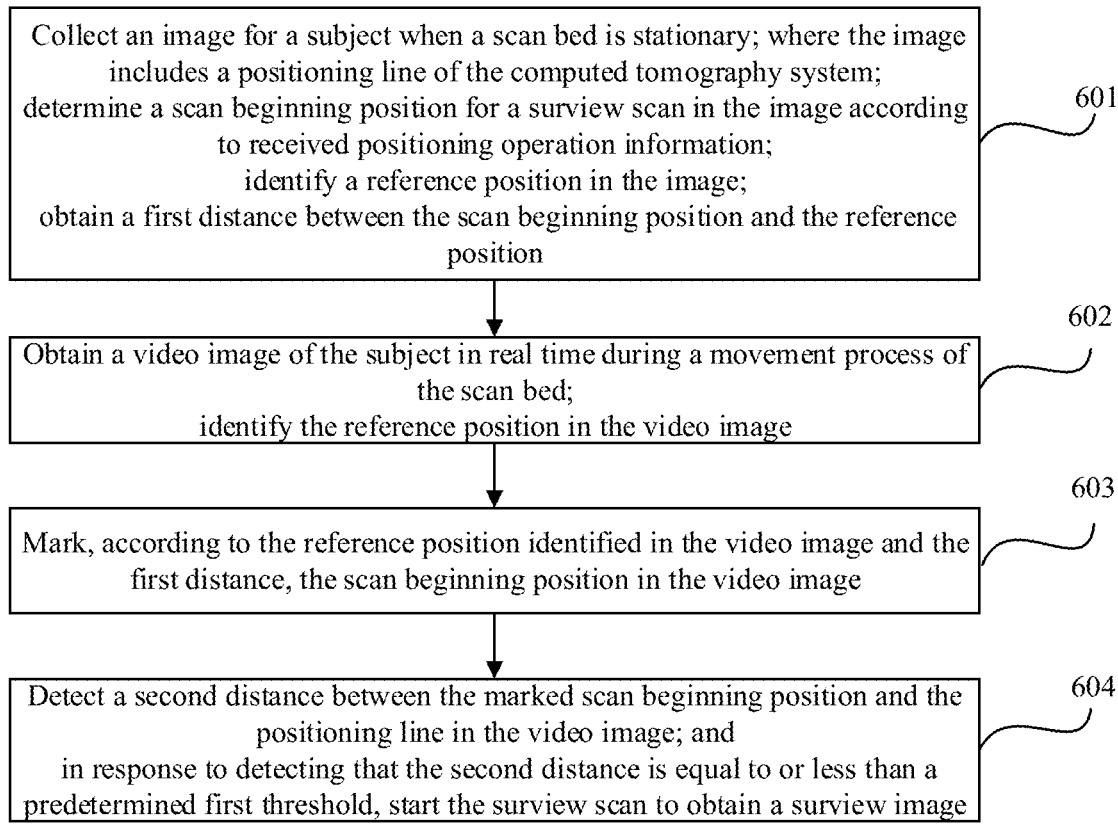
FIG. 6 is an example flowchart illustrating a process of a method of surview scan according to one or more embodiments of the present disclosure.

FIG. 6 is an example flowchart illustrating a process of a method of survey scan according to one or more embodiments of the present disclosure. The method of survey scan can be applied to a main console in a CT system or a PET-CT system. As shown in FIG. 6, in the embodiment, the process can include steps 601-604. The CT system can be the system 100 of FIG. 1 or the system as illustrated in FIGS. 2-5. The main console can be the main console 110 of FIG. 1 or the main console of FIGS. 2-5. The process can be performed by the main console.

At step 601, when a scan bed is stationary, an image (e.g., a static image) for a subject (e.g., the subject 103) is collected, the image for the subject includes a positioning line (e.g., the positioning line 203 as shown in FIG. 5) of the CT system, and a scan beginning position for survey scan is determined in the image for the subject, e.g., according to received positioning operation information, a reference position is identified in the image, and a first distance between the scan beginning position and the reference position is obtained.

At step 602, a video image of the subject is obtained in real time during a movement process of the scan bed, and the reference position is identified in the video image.

At step 603, according to the reference position identified in the video image and the first distance, the scan beginning position is marked in the video image.

At step 604, a second distance between the marked scan beginning position and the positioning line in the video image is detected, and in response to detecting that the second distance is equal to or less than a predetermined first threshold, the survey scan is started to obtain a survey image.

The positioning operation information can be input by a user. For example, in an application, a user (e.g., operation technician) can click a scan beginning point in a video image of the subject collected in real time based on a to-be-scanned part of the subject and the main console generates a scan indication line (e.g., the scan indication line 202 shown in FIG. 4, 5, or 7) passing through the scan beginning point based on the scan beginning point and takes the scan indication line as the scan beginning position for surview scan. In another embodiment, the positioning operation information can be automatically generated by the system, for example, the main console obtains an instruction for scanning a lung, automatically determines a scan beginning point based on the image for the subject, generates a scan indication line passing through the scan beginning point based on the scan beginning point and takes the scan indication line as the scan beginning position for surview scan. After obtaining the surview image, the CT system can complete position planning for a next tomography or helical scan based on the surview image.

The scan indication line is located in a plane parallel to the scan bed, and the scan indication line is perpendicular to a movement direction of the scan bed.

In an example, the reference position is a center of a face contour of the subject, and identifying the reference position in the video image includes: based on a predetermined face contour recognition algorithm, capturing a face contour of the subject in the video image; determining, according to a pixel coordinate corresponding to the face contour captured in the video image, the position of the center of the face contour as the reference position.

In this embodiment, with a center of a face contour of a subject as a reference position, by detecting the center of the face contour in real time in the video image, the scan beginning position can be redrawn in real time in the video image according to a distance between the center of the face contour and the scan beginning position. In this way, the operation technician does not need to perform manual positioning, thus avoiding direct contact between the operation technician and the subject.

The face contour recognition algorithm can include, for example, an algorithm based on deep learning such as FaceNet algorithm, OpenFace algorithm, insightface algorithm, or DeepID algorithm, or an algorithm based on machine learning and conventional algorithm such as Eigen-Face algorithm, LBP algorithm, or AdaBoost algorithm.

In an example, the reference position is a feature point around the scan beginning position, and identifying the reference position in the video image of the subject obtained in real time in a movement process of the scan bed includes: in the video image, searching for an image region matching a first image, where the first image is an image that is screen-shotted from the image for the subject in advance and includes the feature point; determining, according to a position relationship between the feature point in the first image and a contour of the first image, a position of the feature point in the image region matched with the first image and obtained in the video image.

In this embodiment, with a feature point around the scan beginning position as a reference position, by detecting the feature point around the scan beginning position in real time in the video image, the scan beginning position can be redrawn in real time in the video image based on a distance between the feature point around the scan beginning position and the scan beginning position. In this way, the operation technician does not need to perform manual positioning, thus avoiding direct contact between the operation technician and the subject.

When an image region matching the first image is searched for, an image matching algorithm can be adopted, e.g., gray-based matching algorithm, feature-based matching algorithm and deep-learning-based matching algorithm.

In practical applications, a positioning line in the video image and a scan indication line for indicating the scan beginning position superimposed in the video image can be extracted in real time. No limitation is made to the method of line extraction, for example, the extraction can be performed by using Hough Transform or any other line detection solution.

Through steps 601 and 602, in this embodiment, the scan beginning position (e.g., the scan indication line 202 shown in FIG. 4) can be enabled to move along with movement of the subject in a movement process of the scan bed so as to keep the scan beginning position relative to the patient unchanged. This provides basis for subsequently determining a distance between the scan beginning position and the positioning line and achieving automatic positioning.

In a movement process of the scan bed, the positioning line can be kept, e.g., constantly, at the same position in the video image and does not change its position along with the movement of the scan bed and the change of the video image.

In an example, the method further includes: displaying, in real time, the surview image in the screen of the main console; in response to that the surview image satisfies a predetermined scan requirement, stopping the surview scan.

The predetermined scan requirement can be that a region to be tomography scanned or helical scanned appears completely in the surview image.

In an example, the method further includes: during a movement process of the scan bed, displaying the video image as a global view in the screen of the main console and displaying a collected image of the positioning line as a local view in the screen of the main console.

Figure 7:
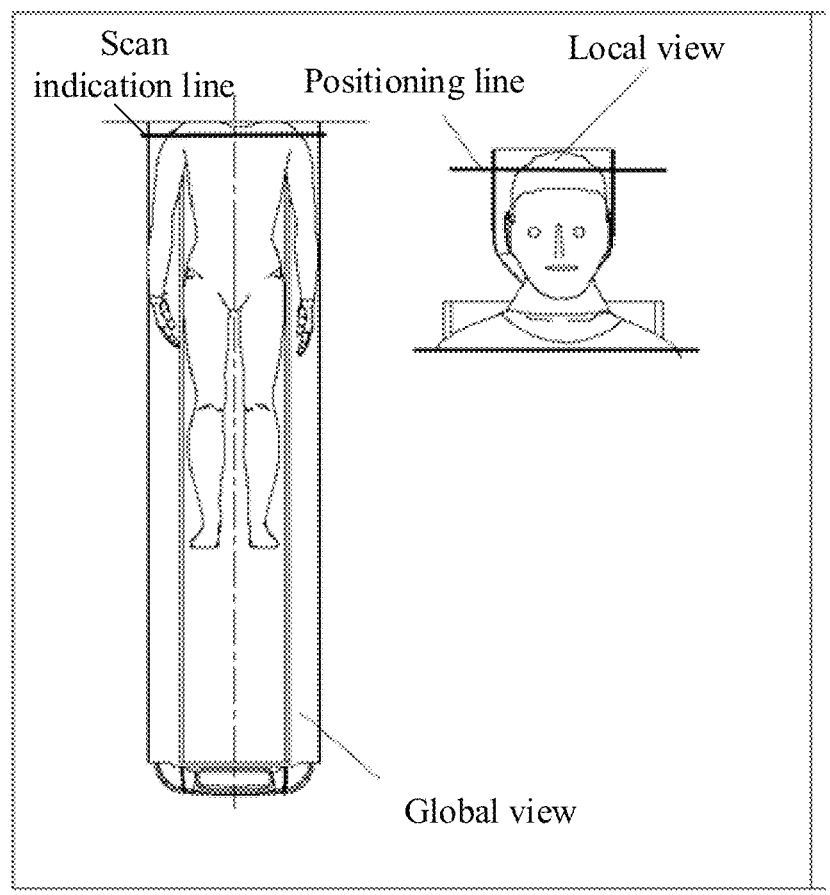
FIG. 7 is a first displaying schematic diagram illustrating a screen of a main console according to one or more embodiments of the present disclosure.

FIG. 7 is a first displaying schematic diagram illustrating a screen of a main console according to one or more embodiments of the present disclosure. As shown in FIG. 7, the video image (global view, e.g., collected by the first camera 108) and the image of the positioning line (local view, e.g., collected by the second camera 109) are displayed in the screen simultaneously, where an enlargement factor of the local view can be greater than that of the global view, so as to ensure the positioning line on the screen can be clearly seen. Further, the local view can also be a picture obtained by enlarging a partial image screen-shotted from the image collected by the first camera.

In an example, during a movement process of the scan bed, when the scan beginning position is close to the positioning line, the scan bed can be slowed down to improve the accuracy of moving the scan beginning position to the positioning line.

In an example, the method further includes: in a surview scan process, displaying the video image as a global view in the screen of the main console and displaying a collected image of the positioning line as a local view in the screen of the main console, and displaying a generated surview image in real time in the screen of the main console.

Figure 8:
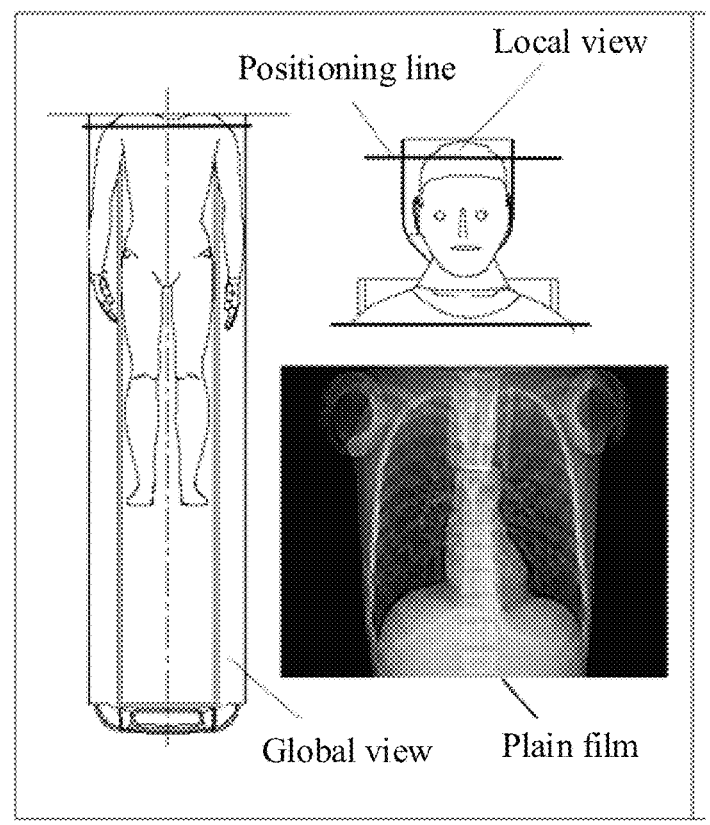
FIG. 8 is a second displaying schematic diagram illustrating a screen of a main console according to one or more embodiments of the present disclosure.

FIG. 8 is a second displaying schematic diagram illustrating a screen of a main console according to one or more embodiments of the present disclosure. As shown in FIG. 8, in a surview scan process, the screen of the main console displays the video image collected by the first camera (e.g., the global view in FIG. 8), the image of the positioning line collected by the second camera (e.g., the locally-enlarged view in FIG. 8) and a surview image obtained by surview scanning (e.g., a plain film in FIG. 8) at the same time.

In this embodiment, the user can observe a state of the subject in real time as well as a state of a generated plain film. In this way, the current surview scan can be completed in time to reduce a radiation dose received by the subject.

In an example, the method further includes: in a tomography scan process after the surview scan is stopped, displaying a surview image as a global view in the screen of the main console, displaying a collected image of the positioning line as a local view in the screen of the main console, and displaying a generated tomogram in real time in the screen of the main console.

Figure 9:
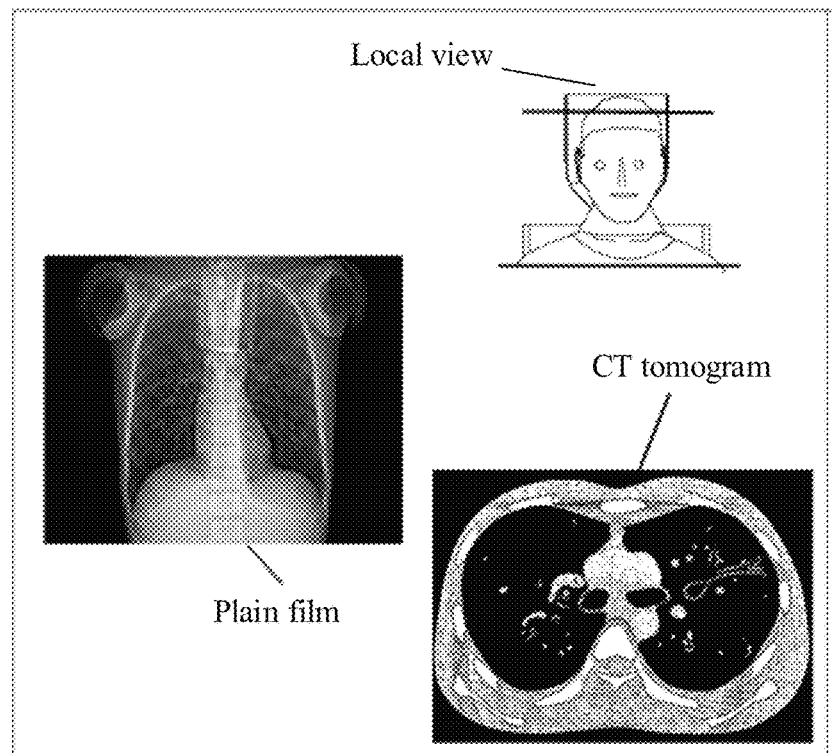
FIG. 9 is a third displaying schematic diagram illustrating a screen of a main console according to one or more embodiments of the present disclosure.

FIG. 9 is a third displaying schematic diagram illustrating a screen of a main console according to one or more embodiments of the present disclosure. As shown in FIG. 9, in a tomography scan process, the screen of the main console displays the surview image (e.g., the plain film in FIG. 9), the image of the positioning line collected by the second camera (locally-enlarged view) and a CT tomogram at the same time.

In this embodiment, the operation technician can observe a state of the subject in real time as well as a generated tomogram. Therefore, in a case of occurrence of abnormal events, the operation technician can interrupt the scan in time to reduce a radiation dose received by the subject.

Referring to step 604 in FIG. 6, the first threshold can be configured according to application requirements. In a scenario of higher accuracy requirement, the first threshold can be configured to a less value, and in a scenario of lower accuracy requirement, the first threshold can be configured to a larger value. For example, in an example, the first threshold can be configured to 50 mm.

In an example, the method can further include: during a movement process of the scan bed, identifying an eye position in real time in the video image; in response to detecting that a third distance between the eye position and the positioning line is less than or equal to a predetermined second threshold, outputting information for prompting the subject to close eyes.

In a scan process, that is, in a movement process of the scan bed, the subject is moved relative to the positioning line. When the eyes of the subject are close to the positioning line, the laser light of the positioning line can be emitted onto the eyes, thus harming the eyes. In this embodiment, the subject can be prompted in time to close eyes so as to reduce harm to the eyes.

The second threshold can be configured or adjusted according to application requirements. For example, in an example, the second threshold can be set to 10 cm.

Based on the above embodiments, in an example, the method further includes: in response to detecting that the third distance between the eye position and the positioning line is less than or equal to a predetermined third threshold and that the subject does not close eyes, turning off a positioning lamp generating the positioning line; where the third threshold is less than the second threshold; in response to detecting that the third distance between the eye position and the positioning line is greater than the third threshold and that the third distance tends to increase, turning on the positioning lamp.

The third threshold can be configured or adjusted according to application requirements. For example, in an example, the third threshold can be set to 2 cm.

For example, when it is detected that the eyes of the subject are 10 cm from the positioning line and continuously approaching the positioning line, the subject can be prompted to close eyes by a voice system of the CT system. If the subject still does not close eyes in a case of about 2 cm from the positioning line, the positioning lamp is turned off and can be turned on again in a case that the eyes move more than 2 cm away from the positioning line.

In this embodiment, when the subject does not close eyes after being prompted to close eyes, the positioning lamp can be turned off actively to reduce harm to the eyes.

It is noted that, in the embodiments of the present disclosure, it is not required to calibrate a camera coordinate system and a CT scan coordinate system, which enables to achieve easy and simple operation.

In a practical operation scenario, an operation technician opens a radiation shielding door of the operation room to allow the subject to enter the scan room on himself while the operation technician stays in the operation room. The operation technician can direct the subject to lie with a desired pose on the scan bed through a bidirectional talkback voice system and close the radiation shielding door remotely after the subject enters the scan room. In this process, the operation technician does not need to enter the scan room, thus reducing potential contact infection.

Afterwards, the operation technician can register the subject on the main console based on a scan examination sheet, or import relevant information of the subject through an information management system of a hospital, so as to complete the input of basic information such as name of the subject and further confirm the accuracy of the relevant information with the subject through the bidirectional voice system.

After completing these preparation works, the operation technician can start a device of a system for surview scan to collect video images of the subject lying on the scan bed in real time and send video images to the main console, and the main console automatically completes surview scan according to the flow of the method of surview scan provided by the embodiments of the present disclosure.

In the embodiments of the present disclosure, each threshold, e.g., the first threshold, the second threshold, or the third threshold, can be determined according to application requirements.

The embodiments of the present disclosure can be applied to a CT system or a PET-CT system.

In the method of surview scan provided by the embodiments of the present disclosure, an image for a subject is collected when a scan bed being stationary, the image includes a positioning line of the computed tomography system, and a scan beginning position for surview scan is determined in the image according to received positioning operation information, a reference position is identified, a first distance between the scan beginning position and the reference position is obtained, and a video image of the subject is obtained in real time during a movement process of the scan bed; in the video image, the reference position is identified, the scan beginning position is marked in the video image according to the reference position identified in the video image and the first distance, a second distance between the scan beginning position marked in the video image and the positioning line is detected, and in response to detecting that the second distance is equal to or less than a predetermined first threshold, surview scan is started to obtain a surview image. By determining the scan beginning position in the video image based on the reference position, the scan beginning position is enabled to always be at a same position of the body of the subject. In this case, the surview scan is completed automatically without requiring the operation technician to enter the scan room to position the subject, thus avoiding contact infection. Therefore, reducing the risk to the health of operation personnel in a surview scan process.

Based on the above method embodiments, an embodiment of the present disclosure further provides corresponding apparatuses, devices and storage media.

Figure 10:
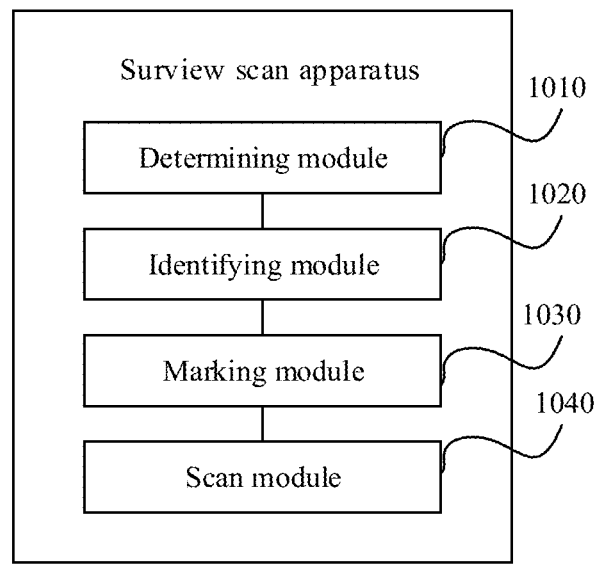
FIG. 10 is a diagram illustrating an apparatus for surview scan according to one or more embodiments of the present disclosure.

FIG. 10 is a functional block diagram illustrating an apparatus for surview scan according to one or more embodiments of the present disclosure. As shown in FIG. 10, in this embodiment, the apparatus can include a determining module 1010, configured to: collect a static image for a subject on a scan bed of the computed tomography system when a scan bed is stationary, where the static image includes a positioning line of the computed tomography system; determine, according to received positioning operation information, a scan beginning position for surview scan in the static image, identify a reference position in the static image as a first reference position, and obtain a first distance between the scan beginning position and the first reference position; an identifying module 1020, configured to: during a movement process of the scan bed, obtain a video image of the subject in real time; identify a reference position in the video image as a second reference position, the reference position in the video image corresponding to the reference position in the static image; a marking module 1030, configured to: mark, according to the second reference position and the first distance, a scan beginning position in the video image as a second scan beginning position, the scan beginning position in the video image corresponding to the scan beginning position in the static image; a scan module 1040, configured to: detect a second distance between the second scan beginning position and a positioning line in the video image that corresponds to the positioning line in the static image, and in response to detecting that the second distance is equal to or less than a predetermined first threshold, start the surview scan to obtain a surview image.

In an example, the reference position in the static image includes a center of a face contour of the subject; the identifying module 1020 is configured to: capture, based on a predetermined face contour recognition algorithm, a face contour of the subject in the video image; determine, according to pixel coordinates corresponding to the face contour captured in the video image, the position of the center of the face contour as the reference position.

In an example, the reference position in the static image comprises a feature point around the scan beginning position; the identifying module 1020 is configured to: search in the video image, for an image region matching a first image that is part of the static image including the feature point; determine, according to a position relationship between the feature point in the first image and a contour of the first image, a position of the feature point in the image region matched the first image and obtained in the video image.

In an example, the apparatus further includes: a first displaying module, configured to display, in real time, the surview image in a screen of a main console; and a scan stopping module, configured to, in response to determining that the surview image satisfies a predetermined scan requirement, stop the surview scan.

In an example, the apparatus further includes: an eye recognizing module, configured to, during a movement process of the scan bed, identify an eye position in real time in the video image; a prompting module, configured to, in response to detecting that a third distance between the eye position and the positioning line in the video image is less than or equal to a predetermined second threshold, output information for prompting the subject to close eyes.

In an example, the apparatus further includes: a turning-off module, configured to, in response to detecting that the third distance between the eye position and the positioning line is less than or equal to a predetermined third threshold and that at least one of the eyes of the subject does is open, turn off a positioning lamp generating the positioning line; where the third threshold is less than the second threshold; a turning-on module, configured to, in response to detecting that the third distance between the eye position and the positioning line is greater than the third threshold and that the third distance keeps increasing, turn on the positioning lamp.

In an example, the apparatus further includes: a second displaying module, configured to, during the movement process of the scan bed, display the video image as a global view in the screen of the main console and display a collected image including the positioning line as a local view in the screen of the main console.

In an example, the apparatus further includes: a third displaying module, configured to, during the surview scan, display the video image as a global view in the screen of the main console and display a collected image including the positioning line as a local view in the screen of the main console, and display a generated surview image in real time in the screen of the main console.

In an example, the apparatus further includes: a fourth displaying module, configured to, in a tomography scan process after the surview scan is stopped, display the surview image as a global view in the screen of the main console and display a collected image including the positioning line as a local view in the screen of the main console, and display a generated tomogram in real time in the screen of the main console.

Figure 11:
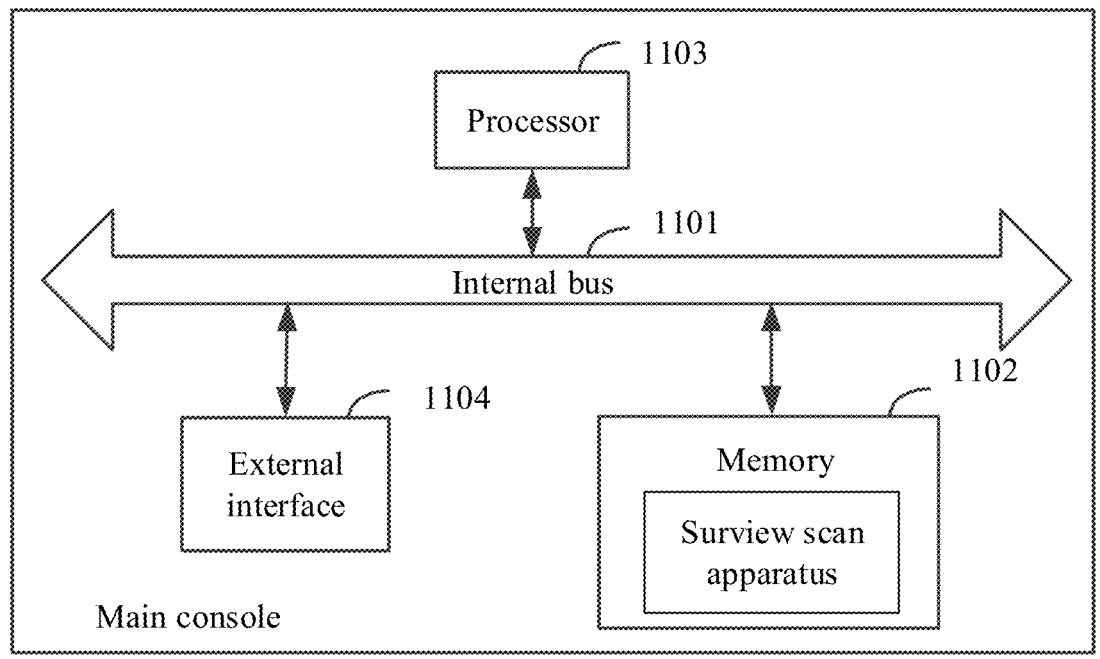
FIG. 11 is a hardware structure diagram illustrating a main console according to one or more embodiments of the present disclosure.

An embodiment of the present disclosure further provides a main console. FIG. 11 is a hardware structure diagram illustrating a main console according to one or more embodiments of the present disclosure. As shown in FIG. 11, the main console includes an internal bus 1101, a memory 1102, a processor 1103 and an external interface 1104, where the memory 1102, the processor 1103 and the external interface 1104 are connected via the internal bus 1101. The memory 1102 are configured to store machine readable instructions corresponding to surview scan logic; the processor 1103 is configured to read the machine readable instructions in the memory 1102 and execute the instructions to perform following operations including: collecting a static image for a subject on a scan bed of the computed tomography system when a scan bed is stationary, where the static image for the subject includes a positioning line of the computed tomography system; determining, according to received positioning operation information, a scan beginning position for surview scan in the static image, identifying a reference position in the static image as a first reference position, and obtaining a first distance between the scan beginning position and the first reference position; during a movement process of the scan bed, obtaining a video image of the subject in real time; identifying a reference position in the video image as a second reference position, the reference position in the video image corresponding to the reference position in the static image; marking, according to the second reference position and the first distance, a scan beginning position in the video image as a second scan beginning position, the scan beginning position in the video image corresponding to the scan beginning position in the static image; detecting a second distance between the marked scan beginning position and a positioning line in the video image that corresponds to the positioning line in the static image; and in response to detecting that the second distance is equal to or less than a predetermined first threshold, starting the surview scan to obtain a surview image.

An embodiment of the present disclosure further provides a computer readable storage medium storing computer programs thereon. The programs are executed by a processor to perform the following operations including: collecting a static image for the subject on a scan bed of the computed tomography system when the scan bed is stationary, where the static image includes a positioning line of the computed tomography system; determining, according to received positioning operation information, a scan beginning position for surview scan in the static image as a first scan beginning position, identifying a reference position in the static image as a first reference position, and obtaining a first distance between the scan beginning position and the first reference position; during a movement process of the scan bed, obtaining a video image of the subject in real time; identifying a reference position in the video image as a second reference position, the reference position in the video image corresponding to the reference position in the static image; marking, according to the second reference position and the first distance, a scan beginning position in the video image as a second scan beginning position, the scan beginning position in the video image corresponding to the scan beginning position in the static image; detecting a second distance between the second scan beginning position and a positioning line in the video image that corresponds to the positioning line in the static image; and in response to detecting that the second distance is equal to or less than a predetermined first threshold, starting the surview scan to obtain a surview image.

Since the apparatus and device embodiments substantially correspond to the method embodiments, a reference can be made to part of the descriptions of the method embodiments for the related part. The apparatus embodiments described above are merely illustrative, where the modules described as separate members can be or not be physically separated, and the members displayed as modules can be or not be physical modules, i.e., can be located in one place, or can be distributed to a plurality of network modules. Part or all of the modules can be selected according to actual requirements to implement the objectives of the solutions in the specification. Those of ordinary skill in the art can understand and carry out them without creative work.

The specific embodiments are described as above. Other embodiments can also be obtained within the scope of the appended claims. In some cases, the actions or steps recorded in the claims can be performed in a sequence different from the embodiments to achieve the desired result. Further, the processes shown in drawings do not necessarily require a particular sequence or a continuous sequence to achieve the desired result. In some implementations, a multi-task processing and parallel processing are possible and can also be advantageous.

Other implementations of the present disclosure will be apparent to those skilled in the art from consideration of the specification and practice of the present disclosure herein. The present disclosure is intended to cover any variations, uses, modification or adaptations of the present disclosure that follow the general principles thereof and include common knowledge or conventional technical means in the related art that are not disclosed in the present disclosure. The specification and embodiments are considered as example only, with a true scope and spirit of the present disclosure indicated by the following claims.

It is to be understood that the present disclosure is not limited to the precise structure described above and shown in the accompanying drawings, and that various modifications and changes can be made without departing from the scope thereof. The scope of the present disclosure is limited only by the appended claims.

The foregoing disclosure is merely illustrative of preferred embodiments of the present disclosure but not intended to limit the present disclosure, and any modifications, equivalent substitutions, adaptations thereof made within the spirit and principles of the present disclosure shall be encompassed in the scope of protection of the present disclosure.

The invention claimed is:

1. A method applied to a computed tomography system, the method comprising:
   collecting a static image for a subject on a scan bed of the computed tomography system when the scan bed is stationary, wherein the static image comprises a positioning line of the computed tomography system;
   determining, according to received positioning operation information, a scan beginning position for a surview scan in the static image as a first scan beginning position;
   identifying a reference position in the static image as a first reference position;
   obtaining a first distance between the scan beginning position and the first reference position;
   during a movement process of the scan bed,
      obtaining a video image of the subject in real time;
      identifying a reference position in the video image as a second reference position, the reference position in the video image corresponding to the reference position in the static image;
      marking, according to the second reference position and the first distance, a scan beginning position in the video image as a second scan beginning position, the scan beginning position in the video image corresponding to the scan beginning position in the static image;
      detecting a second distance between the second scan beginning position and a positioning line in the video image that corresponds to the positioning line in the static image; and
      in response to detecting that the second distance is equal to or less than a predetermined first threshold, starting the surview scan to obtain a surview image.

2. The method of claim 1, wherein the reference position in the static image comprises a center of a face contour of the subject, and
   wherein identifying the reference position in the video image as the second reference position comprises:
      capturing, based on a predetermined face contour recognition algorithm, the face contour of the subject in the video image; and
      determining, according to pixel coordinates corresponding to the face contour captured in the video image, a position of the center of the face contour as the second reference position.

3. The method of claim 1, wherein the reference position in the static image comprises a feature point around the scan beginning position, and
   wherein identifying the reference position in the video image as the second reference position comprises:
      searching, in the video image, for an image region matching a first image that is a part of the static image comprising the feature point; and determining, according to a position relationship between the feature point in the first image and a contour of the first image, a position of the feature point in the image region as the second reference position.

4. The method of claim 1, further comprising:
displaying, in real time, the surview image in a screen of a main console of the computed tomography system; and
in response to determining that the surview image satisfies a predetermined scan requirement, stopping the surview scan.

5. The method of claim 1, further comprising:
during the movement process of the scan bed, identifying an eye position in real time in the video image; and
in response to detecting that a third distance between the eye position and the positioning line in the video image is less than or equal to a predetermined second threshold, outputting information for prompting the subject to close eyes.

6. The method of claim 5, further comprising:
in response to detecting that the third distance between the eye position and the positioning line is less than or equal to a predetermined third threshold and that at least one of the eyes of the subject is open, turning off a positioning lamp generating the positioning line, wherein the third threshold is less than the second threshold; and
in response to detecting that the third distance between the eye position and the positioning line is greater than the third threshold and that the third distance keeps increasing, turning on the positioning lamp.

7. The method of claim 1, further comprising:
during the movement process of the scan bed,
displaying the video image as a global view in a screen of a main console of the computed tomography system, and
displaying a collected image including the positioning line as a local view in the screen of the main console.

8. The method of claim 1, further comprising:
during the surview scan,
displaying the video image as a global view in a screen of a main console of the computed tomography system,
displaying a collected image including the positioning line as a local view in the screen of the main console, and
displaying a generated surview image in real time in the screen of the main console.

9. The method of claim 1, further comprising:
in a tomography scan process after the surview scan is stopped,
displaying the surview image as a global view in a screen of a main console of the computed tomography system,
displaying a collected image including the positioning line as a local view in the screen of the main console, and
displaying a generated tomogram in real time in the screen of the main console.

10. A system, comprising:
a scan bed;
a scan gantry;
a positioning lamp;
a first camera;
a second camera; and
a main console;
wherein the scan gantry is configured to control the scan bed to move according to a control instruction of the main console,
wherein the positioning lamp is configured to generate a positioning line,
wherein the first camera is disposed above the scan bed to collect a video image of a subject on the scan bed and send the video image of the subject to the main console,
wherein the second camera is disposed in a scan bore on the scan gantry to collect a video image of the positioning line and send the video image of the positioning line to the main console, and
wherein the main console is configured to perform operations comprising:
collecting a static image for the subject on the scan bed when the scan bed is stationary, wherein the static image comprises the positioning line;
determining, according to received positioning operation information, a scan beginning position for a surview scan in the static image as a first scan beginning position;
identifying a reference position in the static image as a first reference position;
obtaining a first distance between the scan beginning position and the first reference position in the static image;
during a movement process of the scan bed,
obtaining a video image of the subject in real time;
identifying a reference position in the video image as a second reference position, the reference position in the video image corresponding to the reference position in the static image;
marking, according to the second reference position and the first distance, a scan beginning position in the video image as a second scan beginning position, the scan beginning position in the video image corresponding to the scan beginning position in the static image;
detecting a second distance between the second scan beginning position and a positioning line in the video image that corresponds to the positioning line in the static image; and
in response to detecting that the second distance is equal to or less than a predetermined first threshold, starting the surview scan to obtain a surview image.

11. The system of claim 10, wherein the reference position in the static image comprises a center of a face contour of the subject, and
wherein identifying the reference position in the video image as the second reference position comprises:
capturing, based on a predetermined face contour recognition algorithm, the face contour of the subject in the video image; and
determining, according to pixel coordinates corresponding to the face contour captured in the video image, a position of the center of the face contour as the second reference position.

12. The system of claim 10, wherein the reference position in the static image comprises a feature point around the scan beginning position, and
wherein identifying the reference position in the video image as the second reference position comprises:
searching, in the video image, for an image region matching a first image that is a part of the static image comprising the feature point; and determining, according to a position relationship between the feature point in the first image and a contour of the first image, a position of the feature point in the image region as the second reference position.

13. The system of claim 10, wherein the operations further comprise:
displaying, in real time, the surview image in a screen of the main console; and
in response to determining that the surview image satisfies a predetermined scan requirement, stopping the surview scan.

14. The system of claim 10, wherein the operations further comprise:
during the movement process of the scan bed,
identifying an eye position in real time in the video image; and
in response to detecting that a third distance between the eye position and the positioning line is equal to or less than a predetermined second threshold, outputting information for prompting the subject to close eyes.

15. The system of claim 14, wherein the operations further comprise:
in response to detecting that the third distance between the eye position and the positioning line is equal to or less than a predetermined third threshold and that at least one of the eyes of the subject is open, turning off a positioning lamp generating the positioning line, wherein the third threshold is less than the second threshold; and
in response to detecting that the third distance between the eye position and the positioning line is greater than the third threshold and that the third distance keeps increasing, turning on the positioning lamp.

16. The system of claim 10, wherein the operations further comprise:
during the movement process of the scan bed,
displaying the video image as a global view in a screen of the main console, and
displaying a collected image including the positioning line as a local view in the screen of the main console.

17. The system of claim 10, wherein the operations further comprise:
during the surview scan,
displaying the video image as a global view in a screen of the main console;
displaying a collected image including the positioning line as a local view in the screen of the main console, and
displaying a generated surview image in real time in the screen of the main console.

18. The system of claim 10, wherein the operations further comprise:
in a tomography scan process after the surview scan is stopped,
displaying the surview image as a global view in a screen of the main console;
displaying a collected image including the positioning line as a local view in the screen of the main console, and
displaying a generated tomogram in real time in the screen of the main console.

19. An electronic device, comprising:
at least one processor; and
one or more memories coupled to the at least one processor and storing programming instructions for execution by the at least one processor to perform operations comprising:
collecting a static image for a subject on a scan bed of a computed tomography system when the scan bed is stationary, wherein the static image comprises a positioning line of the computed tomography system;
determining, according to received positioning operation information, a scan beginning position for surview scan in the static image as a first scan beginning position;
identifying a reference position in the static image as a first reference position;
obtaining a first distance between the scan beginning position and the first reference position;
during a movement process of the scan bed,
obtaining a video image of the subject in real time;
identifying a reference position in the video image as a second reference position, the reference position in the video image corresponding to the reference position in the static image;
marking, according to the second reference position and the first distance, a scan beginning position in the video image as a second scan beginning position, the scan beginning position in the video image corresponding to the scan beginning position in the static image;
detecting a second distance between the second scan beginning position and a positioning line in the video image that corresponds to the positioning line in the static image; and
in response to detecting that the second distance is equal to or less than a predetermined first threshold, starting the surview scan to obtain a surview image.

20. The electronic device of claim 19, wherein the operations further comprise at least one of:
during the movement process of the scan bed, displaying the video image as a global view in a screen of the main console, and displaying a collected image including the positioning line as a local view in the screen of the main console,
during the surview scan, displaying the video image as the global view in the screen of the main console, displaying the collected image including the positioning line as the local view in the screen of the main console, and displaying a generated surview image in real time in the screen of the main console, or
in a tomography scan process after the surview scan is stopped, displaying the surview image as the global view in the screen of the main console, displaying the collected image including the positioning line as the local view in the screen of the main console, and displaying a generated tomogram in real time in the screen of the main console.

* * * * *